(12) United States Patent
Sato

(10) Patent No.: US 9,047,395 B2
(45) Date of Patent: Jun. 2, 2015

(54) ENDOSCOPE APPARATUS AND METHOD FOR STORING ENDOSCOPIC IMAGE

(75) Inventor: Saichi Sato, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 462 days.

(21) Appl. No.: 13/342,586

(22) Filed: Jan. 3, 2012

(65) Prior Publication Data

US 2012/0169857 A1    Jul. 5, 2012

Related U.S. Application Data

(60) Provisional application No. 61/429,801, filed on Jan. 5, 2011.

(51) Int. Cl.
*H04N 7/18* (2006.01)
*G06F 19/00* (2011.01)
*A61B 1/00* (2006.01)

(52) U.S. Cl.
CPC ........... *G06F 19/321* (2013.01); *A61B 1/00004* (2013.01)

(58) Field of Classification Search
None
See application file for complete search history.

(56) References Cited

U.S. PATENT DOCUMENTS

2007/0226258 A1*   9/2007   Lambdin et al. ........... 707/104.1
2008/0242986 A1*   10/2008  Ichikawa ...................... 600/443

FOREIGN PATENT DOCUMENTS

JP           2003-009057 A      1/2003

* cited by examiner

*Primary Examiner* — Heather Jones
(74) *Attorney, Agent, or Firm* — Holtz, Holtz, Goodman & Chick PC

(57) ABSTRACT

An endoscope apparatus has an LCD which displays an endoscopic image, and an operation section. The endoscope apparatus stores an endoscopic image in a storage destination folder which is set as a storage destination for the endoscopic image from a plurality of folders which are created in a storage device in advance, displays information indicating the storage destination folder in a state in which the endoscopic image is displayed in the display section, and changes the storage destination folder in response to an operation of the operation section.

23 Claims, 8 Drawing Sheets

ENDOSCOPE APPARATUS AND METHOD FOR STORING ENDOSCOPIC IMAGE

BACKGROUND OF THE INVENTION

1. Field of the Invention

The present invention relates to an endoscope apparatus and a method for storing an endoscopic image.

2. Description of Related Art

Conventionally, endoscope apparatuses have been widely used in the industrial field and the medical field. An endoscope apparatus has an insertion portion having an image pickup unit provided at a distal end portion, and a user who is an inspector brings the distal end portion of the insertion portion close to an object, causes the image which is picked up by the image pickup unit at the distal end portion of the insertion portion to be displayed on the monitor, and can cause the image to be stored in a storage device in accordance with necessity. For example, the user can connect the storage device such as a USB memory to a main body and can store an endoscopic image in the storage device.

In a conventional endoscope apparatus, as disclosed in Japanese Patent Application Laid-Open Publication No. 2003-9057, a DCIM directory is automatically created in a root directory in the storage device in accordance with the DCF standard, and endoscopic images are automatically stored under the directory.

SUMMARY OF THE INVENTION

An endoscope apparatus of one aspect of the present invention has a display section which displays an endoscopic image, an operation section, a storage section which stores the endoscopic image in a storage destination folder which is set as a storage destination for the endoscopic image from a plurality of folders which are created in a storage device in advance, a storage destination folder information display section which displays information indicating the storage destination folder in a state in which the endoscopic image is displayed in the display section, and a storage destination folder changing section which changes the storage destination folder in response to an operation of the operation section.

DETAILED DESCRIPTION OF PREFERRED EMBODIMENT

Hereinafter, an embodiment of the present invention will be described with reference to the drawings.

(Entire Configuration)

Figure 1:
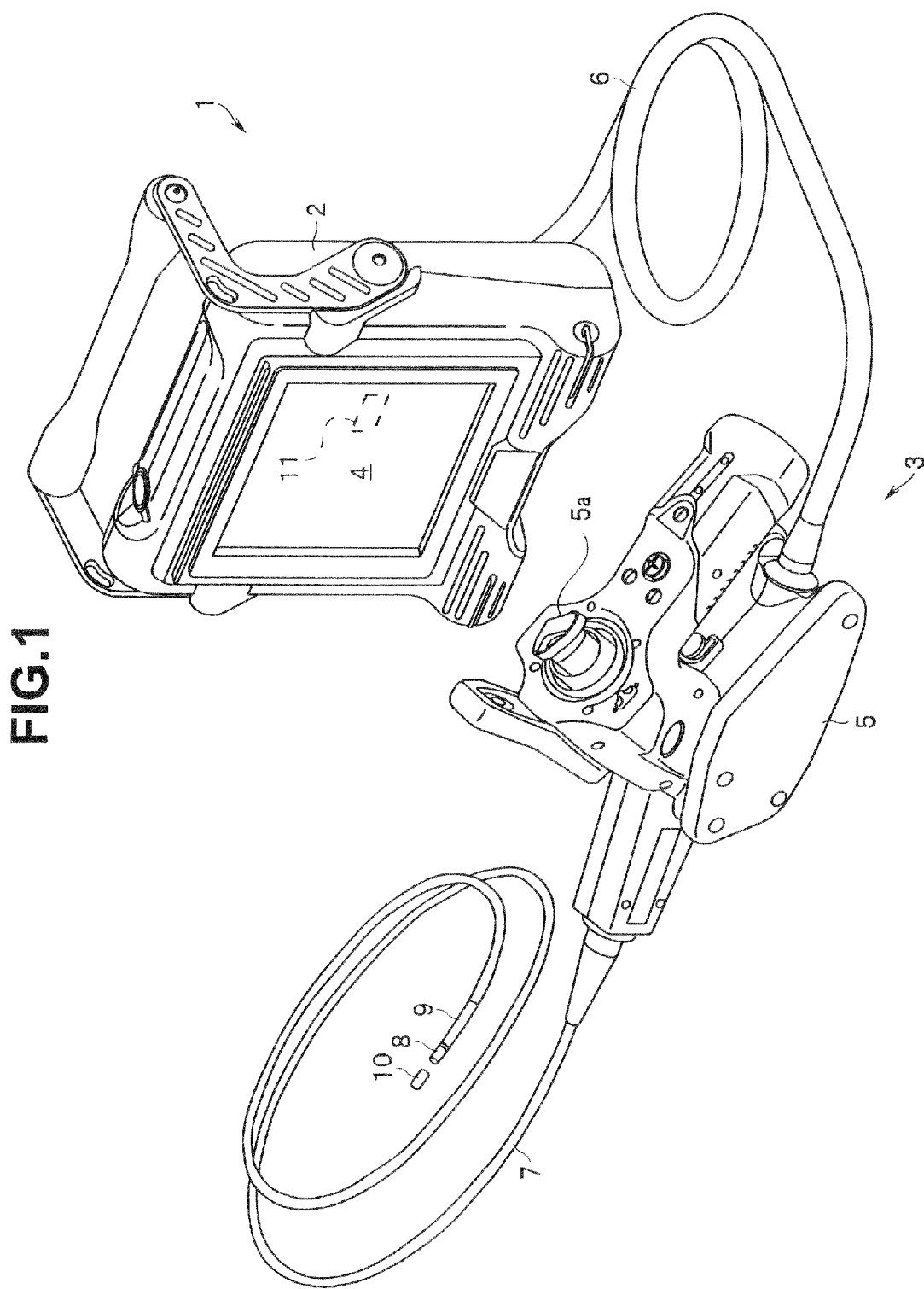
FIG. 1 is an external configuration view of an endoscope apparatus according to an embodiment of the present invention.

First, based on FIG. 1, a configuration of an endoscope apparatus according to the present embodiment will be described. FIG. 1 is an external configuration view of the endoscope apparatus according to the present embodiment.

Figure 2:
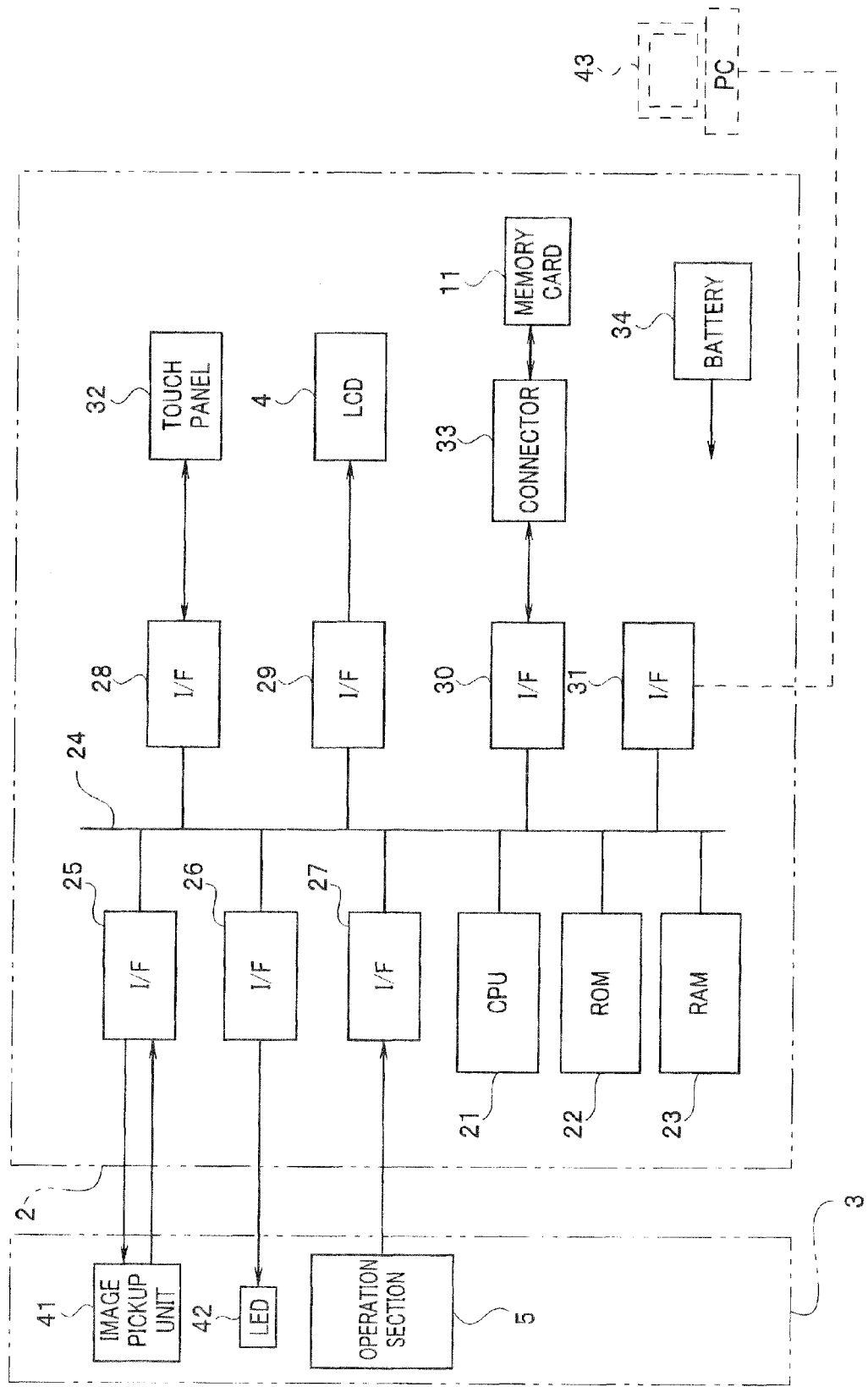
FIG. 2 is a block diagram for explaining a circuit configuration of an inside of a main body section 2 of an endoscope apparatus 1 according to the embodiment of the present invention.

As shown in FIG. 1, an endoscope apparatus 1 is configured to include a main body section 2 which is a main unit, and a scope unit 3 which is connected to the main body section 2. The main body section 2 has a liquid crystal display (hereinafter, abbreviated as an LCD) 4 as a display apparatus in which an endoscopic image, an operation menu and the like are displayed. The LCD 4 is a display section which displays an endoscopic image. As will be described later, the LCD 4 may be provided with a touch panel (FIG. 2). The scope unit 3 has an operation section 5 which is connected to the main body section 2 by a universal cable 6 which is a connection cable, and an insertion portion 7 which is connected to the operation section 5 and includes a flexible insertion tube. The scope unit 3 is attachable to and detachable from the main body section 2. An image pickup unit (FIG. 2) which will be described later is contained in a distal end portion 8 of the insertion portion 7. The image pickup unit is configured by an image pickup device such as a CCD sensor or a CMOS sensor, for example, and an image pickup optical system such as a lens which is disposed at an image pickup surface side of the image pickup device. A bending portion 9 is provided at a proximal end side of the distal end portion 8. An optical adapter 10 is configured to be attachable to the distal end portion 8. The operation section 5 is provided with various operation buttons such as a freeze button, a storage instruction button (hereinafter, REC button), and an up, down, left and right (U/D/L/R) direction bending button.

A user can perform image pickup of an object, still image storage and the like by operating the various operation buttons of the operation section 5. Further, the user can select a storage destination folder by performing an operation of tilting a joystick 5a provided at the operation section 5 in any one of up, down, left and right directions, when the user performs change of the storage destination folder for an endoscopic image, which will be described later. Further, in the case of the configuration in which a touch panel is provided at the LCD 4, the user can give instructions of various operations of the endoscope apparatus 1 by operating the touch panel. More specifically, the touch panel configures an instruction section which gives an instruction on the operation content of the endoscope apparatus 1.

The image data of the endoscopic image which is picked up and obtained is inspection data of an inspection target, and is stored in a memory card 11. The memory card 11 is attachable to and detachable from the main body section 2.

In the present embodiment, image data is stored in the memory card 11 as a storage medium attachable to and detachable from the main body section 2, but the image data may be stored in a memory contained in the main body section 2.

The user can bring the distal end portion 8 of the insertion portion 7 to a site to be inspected of an inspection target, pick up the site to be inspected, obtain an endoscopic image, and display the endoscopic image on the LCD 4. Further, as will be described later, the user can change the storage destination folder for endoscopic images while confirming the folder in the memory card 11 which stores the endoscopic images at the time of inspection, and operating the operation section 5 if necessary.

(Circuit Configuration)

FIG. 2 is a block diagram for explaining a circuit configuration of an inside of the main body section 2 of the endoscope apparatus 1.

The main body section 2 includes a central processing unit (hereinafter, called a CPU) 21, a ROM 22 and a RAM 23, which are connected to one another through a bus 24. Further, a plurality of various interfaces (hereinafter, called I/Fs) 25 to 31 are connected to the bus 24. The I/F 25 is a drive and receiving circuit for performing transmission of a drive signal to an image pickup unit 41 of the scope 3, and reception of an image pickup signal from the image pickup unit 41. The I/F 26 is a drive circuit for transmitting a drive signal to an LED 42 as an illumination section.

The I/F 27 is a circuit for receiving various operation signals from the operation section 5. Various operation signals from the operation section 5 include an operation signal of a joystick 5a. In the case of the configuration in which the touch panel 32 is provided at the LCD 4, the I/F 28 is provided as a circuit for receiving a drive signal to the touch panel 32 and an operation signal from the touch panel 32. The I/F 29 is a circuit for supplying an image signal to the LCD 4.

The I/F 30 is a circuit for performing write of an image signal to the memory card 11 and read of an image signal from the memory card 11. The I/F 30 is connected to the memory card 11 via a connector 33 provided at the main body section 2. The memory card 11 is attachably and detachably fitted to the connector 33.

The I/F 31 is a circuit for connecting a personal computer (hereinafter, called a PC) 43, which is an external apparatus, to the main body section 2. The PC 43 is connected to the main body section 2 via a connector not illustrated, and the main body section 2 can exchange data with the PC 43 via the I/F 31 which is connected to the connector.

The main body section 2 contains a battery 34 in an inside thereof, and the battery 34 supplies power to various circuits in the main body section 2.

Each of the I/Fs operates under control of the CPU 21. When the endoscope apparatus 1 is actuated, the CPU 21 outputs various drive signals to the image pickup unit 41 via the I/F 25, and the image pickup unit 41 outputs an image pickup signal to the CPU 21. The CPU 21 outputs a drive instruction signal for the LED 42 to the I/F 26, and the LED 42 is driven by the output of the I/F 26, and illuminates the object, as a result of which, a live image is displayed on the LCD 4.

Since the operation section 5 is connected to the CPU 21 via the I/F 27, the operation section 5 supplies, to the CPU 21, various operation signals indicating the operation contents by the user to the operation section 5. When the user depresses the freeze button as will be described later, the CPU 21 generates a still image based on the image pickup signal from the image pickup unit 41, and when the user further depresses the REC button, the image data of the still image is stored in the memory card 11. Since the still image by freeze is displayed on the LCD 4, the user can confirm the still image, and when the user stores the still image, the user depresses the REC button.

(Folder Configuration)

A user can create an optional folder in the memory card 11. For example, the user creates a plurality of folders having a hierarchical structure in the memory card 11 by using a PC before endoscope inspection. More specifically, the user can create a plurality of folders with desired folder names under "root", and can cause each of the folders to store endoscopic images. Further, folders can be further created under the upper folders. More specifically, the user can create the folders having a hierarchical structure in the storage medium. Subsequently, as will be described later, the user can store, in a desired folder, the endoscopic image which is picked up and obtained by the image pickup unit 41 of the scope 3.

Figure 3:
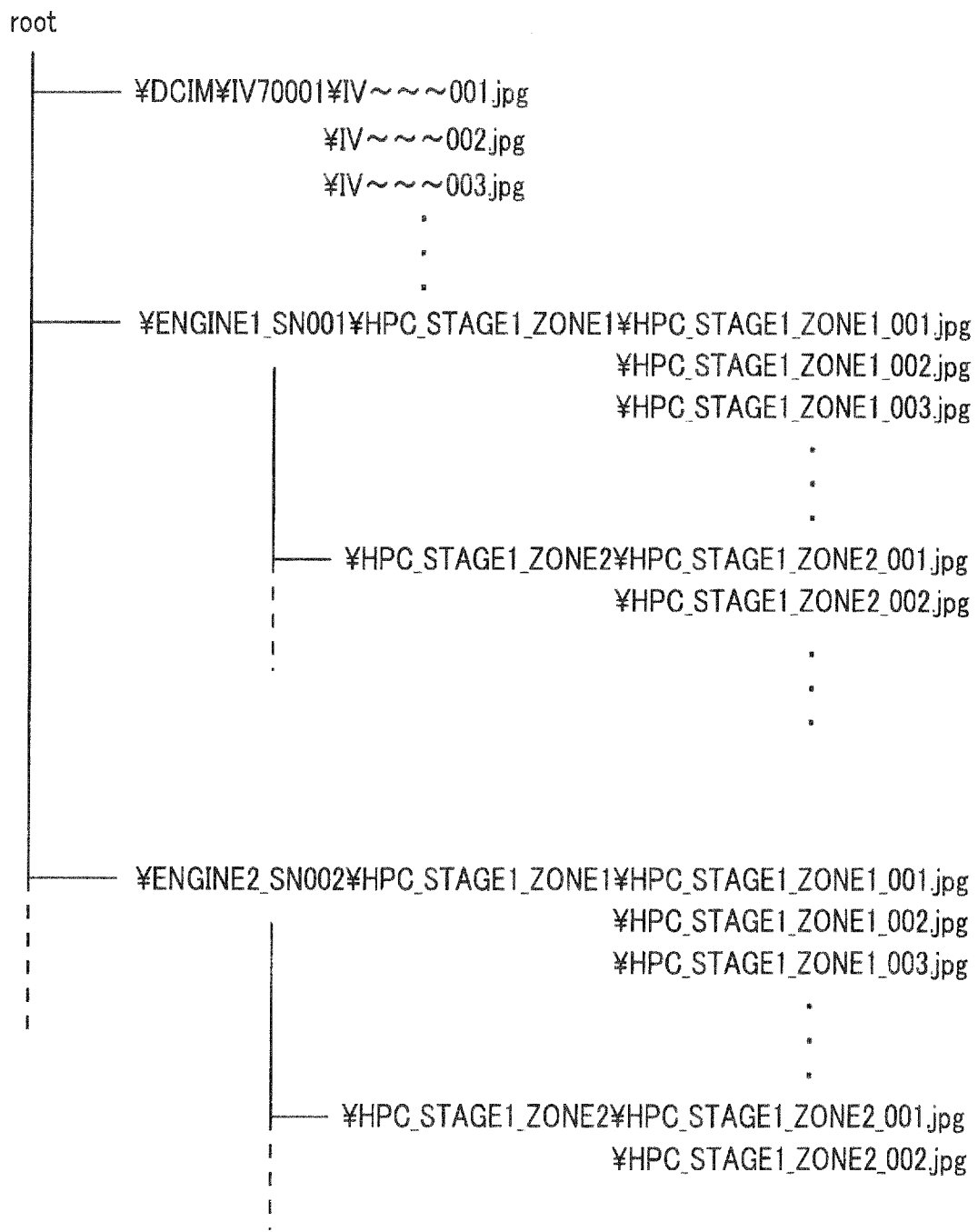
FIG. 3 is a diagram for explaining an example of a folder of a hierarchical structure according to the embodiment of the present invention.

FIG. 3 is a diagram for explaining an example of folders of a hierarchical structure. FIG. 3 schematically represents respective folders and files included in the folders in order to explain the folders of a hierarchical structure, and here, FIG. 3 shows an example of the folders having two hierarchical layers, that is, two levels.

As shown in FIG. 3, a folder "DCIM" is located under "root", and a lower folder named "IV70001" is located under the folder "DCIM".

Further, a folder "ENGINE1_SN001" is created under "root", and two lower folders named "HPC_STAGE1_ZONE1" and "HPC_STAGE1_ZONE2" are created under the folder "ENGINE1_SN001".

Furthermore, under "root", a folder "ENGINE1_SN002" is also created, and under the folder "ENGINE2_SN002", two lower folders named "HPC_STAGE1_ZONE1" and "HPC_STAGE1_ZONE2" are created.

The three folders "DCIM", "ENGINE1_SN001" and "ENGINE2_SN002" of the upper hierarchical layer are the folders of the same hierarchical layer. The folder "ENGINE1_SN001" (and the folder "ENGINE2_SN002") and the folder "HPC_STAGE1_ZONE1" (and the folder "HPC_STAGE1_ZONE2") are the folders of the hierarchical layers different from each other.

More specifically, the user creates and registers a folder with an optional name in advance under "root" in the memory card 11. The user may perform the folder creating work with an external apparatus such as the PC 43, or may perform the folder creating work by connecting a hardware keyboard to the endoscope apparatus 1 and operating the hardware keyboard. Further, the user may perform the folder creating work by operating a setting screen displayed on the LCD 4 and a software keyboard which is configured as GUI. Furthermore, in the case of the configuration in which the touch panel 32 is provided at the LCD 4, the user may perform the folder creating work by operating the touch panel 32 or the like, by using the setting screen displayed on the LCD 4. As will be described later, the user selects an optional folder from a plurality of folders which are created in advance like this as a storage destination folder for endoscopic images, and can store the obtained endoscopic images in the selected folder.

In the present embodiment, the number of the folder hierarchical layers is two, but as shown by the dotted lines in FIG. 3, the number of the folder hierarchical layers may be three or more, and the number of folders of the same hierarchical layer may be three or more. Further, the number of the folder hierarchical layers does not have to be always two or more, and the folder structure with only one hierarchical layer under "root" may be adopted.

Furthermore, in FIG. 3, two folders have the lower folder name of "HPC_STAGE1_ZONE1", but the upper folders of the two folders differ from each other, and therefore, there is no problem even the two folders have the same folder name. Note that on the same hierarchical layer, that is, in the same hierarchical layer, the same folder name cannot be given to a plurality of folders.

As shown in FIG. 3, a plurality of endoscopic images in a JPEG format are shown to be stored in two folders "HPC_STAGE1_ZONE1" and "HPC_STAGE1_ZONE2".

The file name of the endoscopic image is made by addition of a serial number to the folder name, but the file name of the endoscopic image may be only a serial number.

Furthermore, in the case of FIG. 3, the file name is the one having a serial number added to the folder name of the lower hierarchical layer, but the file name may be the one that has a serial number added to the folder names of the upper and lower hierarchical layers. More specifically, the file name may be made "upper folder name_lower folder name_serial number.jpg". For example, the folder name of "ENGINE1_SN001" of the upper folder and the folder name of "HPC_STAGE1_ZONE1" of the lower folder are connected with an under bar, a serial number is further added, and the file name as "ENGINE1_SN001_HPC_STAGE1_ZONE1_001.jpg" may be generated.

Furthermore, the under bars of the folder name and the file name are not necessarily used, but the user can arbitrarily use an under bar in accordance with the kinds of a subject and inspection. More specifically, an optional number, that is, zero or more, of under bars are used.

(Screen Display)

Figure 4:
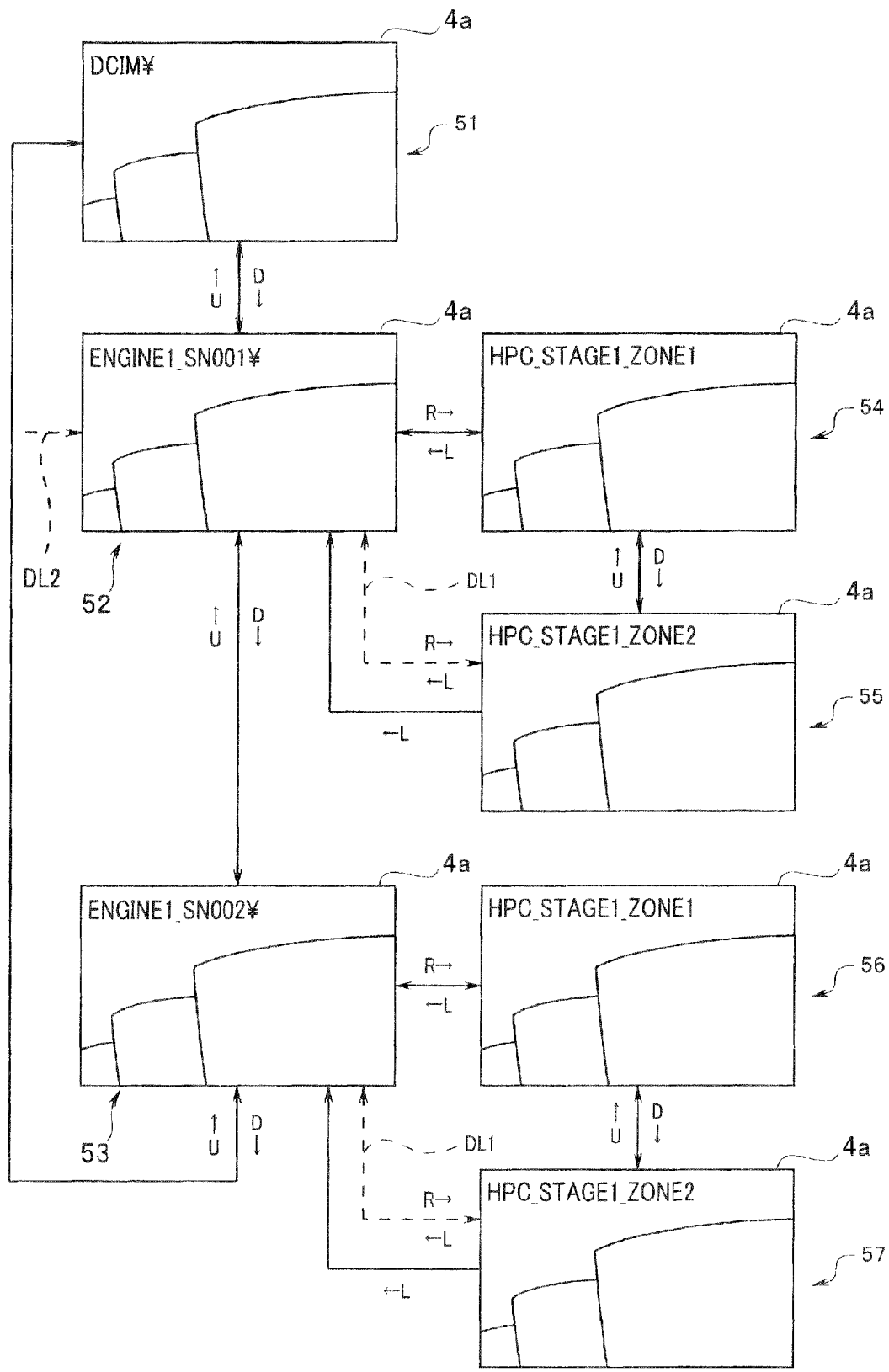
FIG. 4 is a diagram for explaining transition of screen display at a time of change of a storage destination folder, according to the embodiment of the present invention.

Next, screen display at a time of change of the storage destination folder will be described. FIG. 4 is a diagram for explaining a transition of screen display at the time of change of the storage destination folder.

When the power supply of the endoscope apparatus 1 is turned ON, a live image of a target picked up by the image pickup unit 41 is displayed on the screen of the LCD 4. The user performs inspection while watching the live image of the inspection target (turbine blade in FIG. 4) displayed on the screen.

On a screen 4a of the LCD 4, the live image, and the storage destination folder name for the image are displayed. After the power supply is turned ON, the "DCIM" folder under "root" is set in advance as the storage destination folder. Therefore, as shown in a screen 51, directly after the power supply is turned ON, "DCIM¥" is displayed on the screen 4a as the storage destination folder.

On the screen 51 of FIG. 4, information "DCIM¥" which shows that the storage destination folder is the folder "DCIM" is displayed at an upper left side of the screen 4a. On other screens 52 and the like, information including the storage destination folder names is also displayed at upper left sides of the screens 4a. However, the position of the information does not have to be the upper left side of the screen, and may be at an upper right side, for example.

Furthermore, in the case of FIG. 4, mark "¥" is added to the folder names of the storage destination folders in the screens 51, 52 and 53 as the information indicating the storage destination folders. However, the mark "¥" does not have to be added.

Further, in the case of FIG. 4, the information indicating the storage destination folder is the information including the folder name of the storage destination folder. However, if the user can recognize and discriminate the storage destination folder, the information indicating the storage destination folder does not have to include the folder name of the storage destination folder.

When the user desires to store a still image in the desired folder which is created in advance, the user can select the folder by operating the joystick 5a. When the joystick 5a is tilted in any one of the directions of up (U), down (D), left (L) and right (R), the folder is selected from a plurality of folders of the hierarchical structure in accordance with the direction, and is set as the storage destination folder.

FIG. 4 represents the screen transition when the storage destination folder is selected from the folder group having two hierarchical layers shown in FIG. 3 and having two folders created under each of the hierarchical layers. The order of display of the storage destination folders in each of the hierarchical layers is set in advance so that display is performed in a predetermined order such as the order of the creation dates and times of folders, the alphabetic order of the folder names, and the like.

As shown in FIG. 4, when the joystick 5a is tilted down (that is, tilted in the D direction) from the state of the screen 51, the folder "ENGINE1_SN001" which is the next folder (folder under the folder "DCIM", in FIG. 3) of the same hierarchical layer is selected as the storage destination folder, and the screen transitions to the screen 52 from the screen 51.

When the joystick 5a is tilted up (that is, tilted in the U direction) in the state of the screen 52, the folder "DCIM" which is the previous folder of the same hierarchical layer (folder which is upper from the folder "ENGINE1_SN001" in FIG. 3) is selected as the storage destination folder, and the screen transitions to the screen 51 from the screen 57.

When the joystick 5a is tilted down (that is, tilted in the D direction) from the state of the screen 52, the folder "ENGINE2_SN002" which is the next folder of the same hierarchical layer is selected as the storage destination folder, and the screen transitions to a screen 53 from the screen 52.

When the joystick 5a is tilted down (that is, tilted in the D direction) from the state of the screen 53, the folder "DCIM" which is the first folder of the same hierarchical layer is selected as the storage destination folder, and the screen transitions to the screen 51 from the screen 53.

Further, when the joystick 5a is tilted to the right (that is, tilted in an R direction) in the state of the screen 52, the folder "HPC_STAGE1_ZONE1" which is the first folder (the uppermost folder in FIG. 3) of the lower hierarchical layer is selected as the storage destination folder, and the screen transitions to a screen 54 from the screen 52.

Furthermore, when the joystick 5a is tilted to the left (more specifically, tilted in an L direction) in the state of the screen 54, the folder "ENGINE1_SN001" which is the folder of the upper hierarchical layer is selected as the storage destination folder, and the screen transitions to the screen 52 from the screen 54.

When the joystick 5a is tilted down (that is, tilted in the D direction) from the state of the screen 54, the folder "HPC_STAGE1_ZONE2" which is the next folder of the same hierarchical layer is selected as the storage destination folder, and the screen transitions to a screen 55 from the screen 54.

When the joystick 5a is tilted up (that is, tilted in the U direction) in the state of the screen 55, the folder "HPC_STAGE1_ZONE1" which is the previous folder of the same hierarchical layer is selected as the storage destination folder, and the screen transitions to the screen 54 from the screen 55.

Furthermore, when the joystick 5a is tilted to the left (that is, tilted in the L direction) in the state of the screen 55, the folder "ENGINE1_SN001" which is the folder of the upper hierarchical layer is selected as the storage destination folder, and the screen transitions to the screen 52 from the screen 55.

Screen transition among the folder "ENGINE1_SN002" and the two lower folders "HPC_STAGE1_ZONE1" and "HPC_STAGE1_ZONE2" are performed among the screens 53, 56 and 57 similarly to the screen transition of the screens 52, 54 and 55, as shown in FIG. 4.

Accordingly, the user can confirm the storage destination folder while watching the live image, and can easily perform change.

In the case of FIG. 4, when the joystick 5a is tilted to the right (that is, tilted in the R direction) in the state of the screen 52 or 53, after the screen transitions to the screen 52 or 53 from the screen 55 or 57, the screen transitions to the screen 54 or 56 from the screen 52 or 53 so that the folder "HPC_STAGE1_ZONE1" which is the first folder of the lower hierarchical layer is selected as the storage destination folder. However, when the joystick 5a is tilted to the right (that is, tilted in the R direction) in the state of the screen 52 or 53, after the screen transitions to the screen 52 or 53 from the screen 55 or 57, the screen 55 or 57 may be displayed as shown by a dotted line DL1 in FIG. 4. To this end, the folder data of the transition screen is stored in the RAM 23, and the CPU 21 controls the screen display to display a folder before the transition.

In the case of FIG. 4, the folder "DCIM" is selected or set as the storage destination folder by default, but a predetermined folder in the folder of the uppermost hierarchical layer other than the folder "DCIM", for example the folder "ENGINE1_SN001" as the first folder, may be selected by default.

Furthermore, the storage destination folder may be selected only among the folders other than "DCIM" when shifting to the folder of the same hierarchical layer in the uppermost hierarchical layer. In FIG. 4, when the joystick 5a is tilted down (that is tilted in the D direction) in the state of the screen 53 as shown by a clotted line DL2, the screen may be made to transition to the screen 52. Then, when the joystick 5a is tilted up (that is, tilted in the U direction) in the state of the screen 52, the screen may be made to transition to the screen 53.

In the present embodiment, only the folder name of the hierarchical layer which is selected at present is displayed on the screen, but, for example, when the folder name of the lower hierarchical layer is displayed, the folder name of the hierarchical layer upper from the folder may be displayed in combination. At this time, the folder name in the screen 54, for example, is "ENGINE1_SN001_¥HPC_STAGE1_ZONE1".

(Change Processing of Storage Destination Folder)

Figure 5:
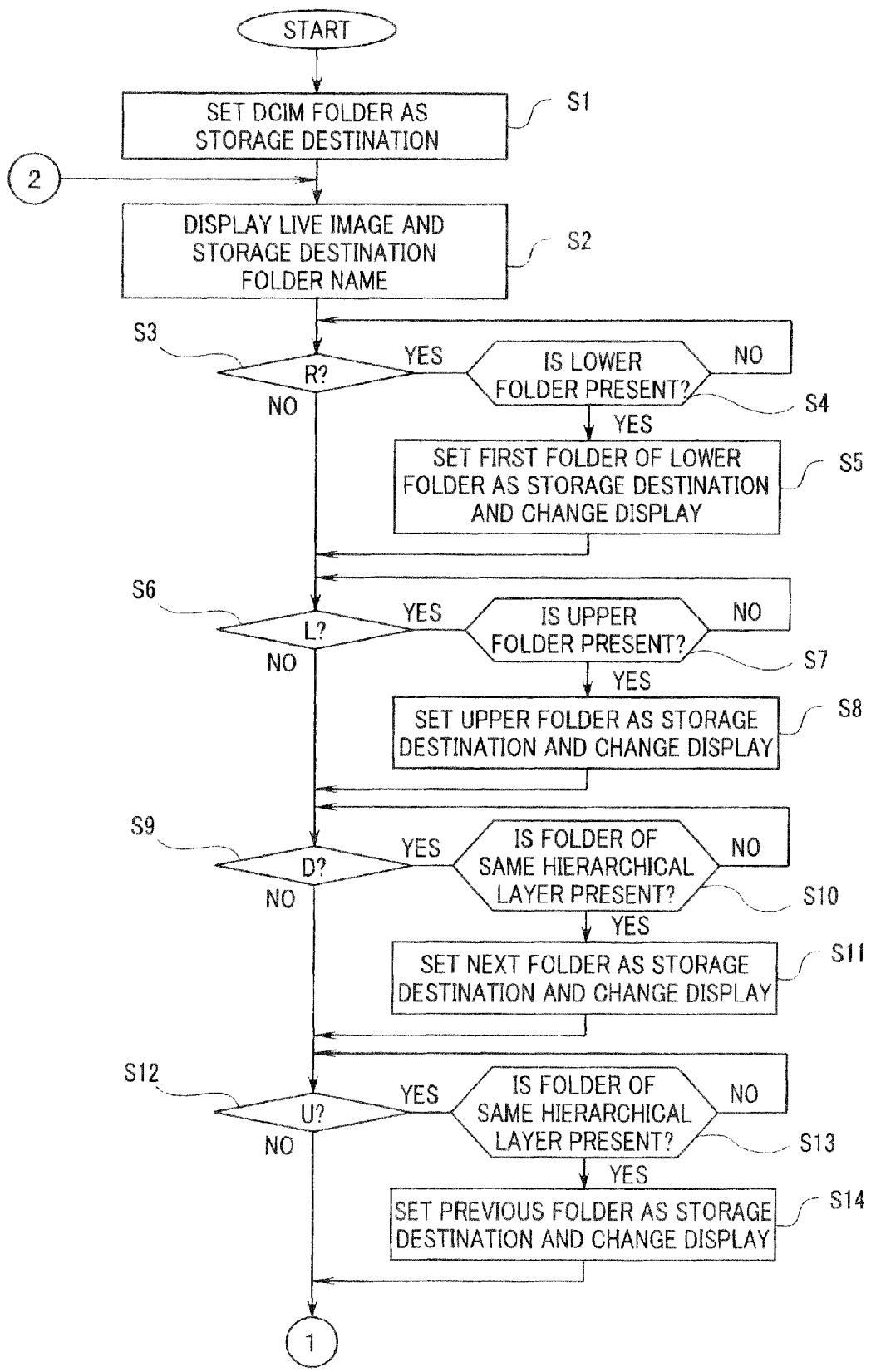
FIG. 5 and FIG. 6 are flowcharts showing an example of a flow of change processing of the storage destination folder according to the embodiment of the present invention.
Figure 6:
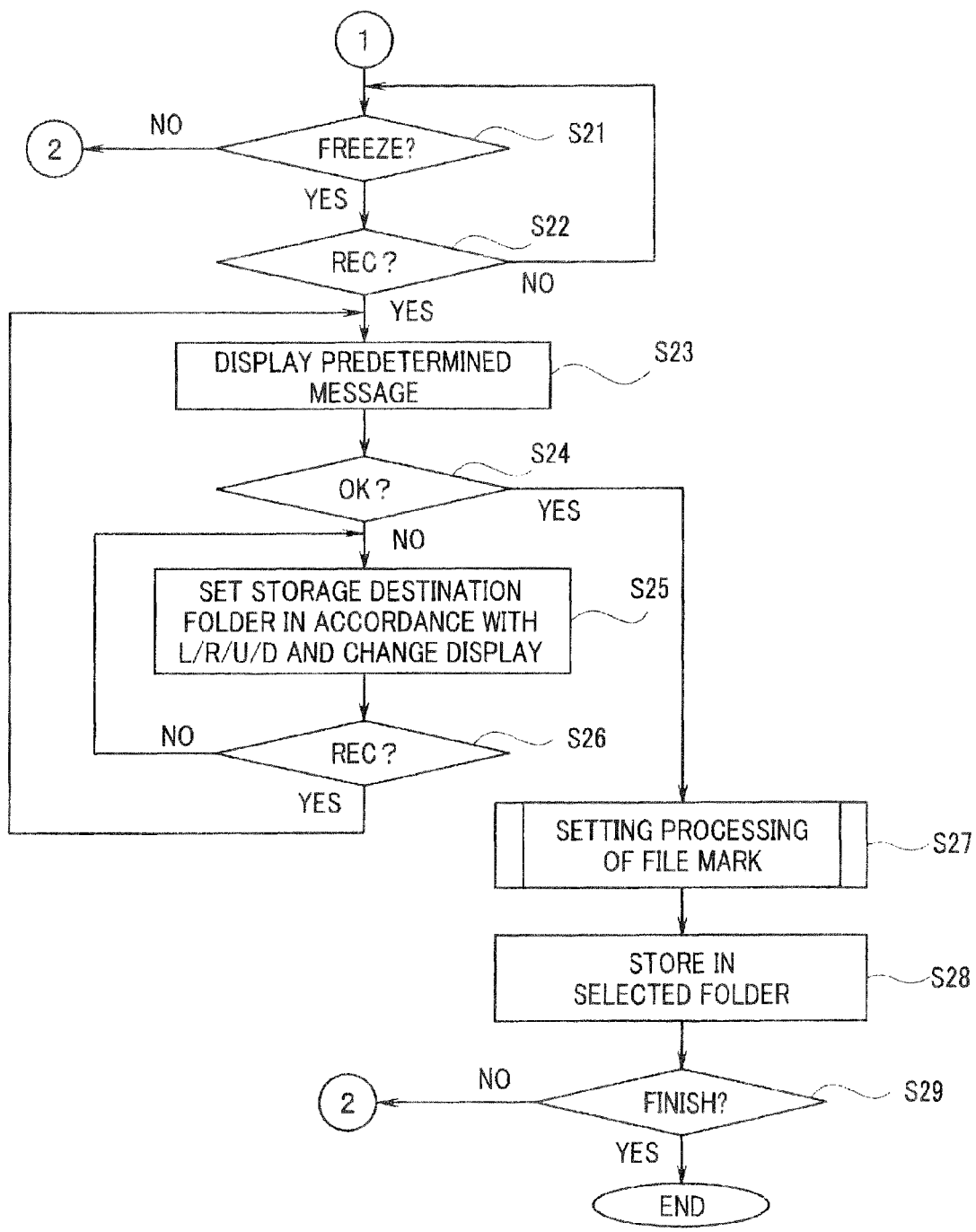

Next, change processing of the aforementioned storage destination folder will be described. FIG. 5 and FIG. 6 are flowcharts showing an example of a flow of the change processing of the storage destination folder.

First, when the power supply of the endoscope apparatus 1 is turned ON, the CPU 21 sets the folder "DCIM", which is the folder determined in advance as default, as the storage destination folder, after executing various kinds of initial processing (S1). The set data is stored in a predetermined storage region of the RAM 23, for example, as the set data of the storage destination folder in image storage processing which the endoscope apparatus has.

Thereafter, the CPU 21 displays a live image and the storage destination folder name on the screen 4a of the LCD 4 as the screen 51, based on the image pickup signal from the image pickup unit 41 (S2). The processing of S2 configures a storage destination folder information display section which displays the information indicating the storage destination folder in the state in which the endoscopic image is displayed on the display section.

Next, the CPU 21 determines whether or not the joystick 5a is tilted in the right (R) direction (S3), and when the joystick 5a is tilted in the right (R) direction (S3: YES), the CPU 21 determines whether or not the present storage destination folder has a lower folder (S4).

When a lower folder which is of a different hierarchical layer is absent (S4: NO), the processing returns to S3. When the lower folder is present (S4: YES), the CPU 21 sets the first folder of the lower folder as the storage destination folder, and changes the display of the storage destination folder name in the screen 4a (S5). Since the information of the storage destination folder is stored in the predetermined storage region of the RAM 23 as described above, the data of the predetermined storage region is rewritten with the data of the set, namely, changed folder.

For example, when the joystick 5a is tilted in the right (R) direction in the state in which the folder "ENGINE1_SN001" is the storage destination folder (screen 52), the "HPC STAGE1 ZONE1" folder which is the first folder of the lower hierarchical layer is set as the storage destination folder. More specifically, the screen transitions from the screen 52 to 54.

A lower folder which is automatically created in accordance with the DCF standard is present in the "DCIM" folder, but the lower folder is not recognized. As a result, the folder "DCIM" is set as the storage destination folder directly after the power supply is turned ON, but even if the joystick 5a is tilled in the right (R) direction in this state (that is, the state of the screen 51), the CPU 21 determines that the lower folder is absent (S4: NO).

In the case of NO in S3, and after the processing of S5, the CPU 21 determines whether or not the joystick 5a is tilted in the left (L) direction (S6), and when the joystick 5a is tilted in the left (L) direction (S6: YES), the CPU 21 determines whether or not an upper folder of the present storage destination folder is present (S7).

When the upper folder which is of a different hierarchical layer is absent (S7: NO), the processing returns to S6. When the upper folder of the present storage destination folder is present (S7: YES), the CPU 21 sets the upper folder as the storage destination folder, and changes display of the storage destination folder name in the screen 4a (S8).

Since the "DCIM" folder, the "ENGINE2_SN001" folder and the "ENGINE2_SN002" do not have an upper folder, the CPU 21 determines that the upper folder is absent even if the joystick 5a is tilted in the left (L) direction in the states of the screens 51, 52 and 53 (S7: NO). Accordingly, in this case, the screens 51, 52 and 53 do not change.

In the case of NO in S6, and after the processing of S8, the CPU 21 determines whether or not the joystick 5a is tilted in the down (D) direction (S9). When the joystick 5a is tilted in the down (D) direction (S9: YES), the CPU 21 determines whether or not the folder of the same hierarchical layer as the present storage destination folder is present (S10).

When the folder of the same hierarchical layer is absent (S10: NO), the processing returns to S9. When the folder of the same hierarchical layer as the present storage destination folder is present (S10: YES), the CPU 21 sets the next folder of the same hierarchical layer as the storage destination folder, and changes display of the storage destination folder name in the screen 4a (S11).

For example, when the joystick 5a is tilted in the down (D) direction in the state in which the "DCIM" folder is the storage destination folder (state of the screen 51), the "ENGINE1_SN001" folder which is the next folder of the same hierarchical layer is set as the storage destination folder. That is to say, the screen transitions from the screen 51 to 52. Further, when the joystick 5a is tilted in the down (D) direction, the "ENGINE2_SN002" folder which is the next folder of the same hierarchical layer is set as the storage destination folder. That is to say, the screen transitions from the screen 52 to 53. Further, when the joystick 5a is tilted in the down (D) direction, the "DCIM" folder which is the first folder of the same hierarchical layer is set as the storage destination folder, display of the storage destination folder in the screen 4a is changed since the next folder of the same hierarchical layer is absent. Then, the screen transitions from the screen 53 to 51.

In the same manner, if the joystick 5a is tilted in the down (D) direction in the state of the screen 54 in which the "HPC_STAGE1_ZONE1" folder is set as the storage destination folder, the screen transitions from the screen 54 to the screen 55 in which the "HPC_STAGE1_ZONE2" folder is set as the storage destination folder. Further when the joystick 5a is tilted in the down (D) direction in the state of the screen 55, the "HPC_STAGE1_ZONE1" folder which is the first folder of the same hierarchical layer is set as the storage destination folder since the next folder of the same hierarchical layer is absent. That is to say, the screen transitions from the screen 55 to 54.

In the case of NO in S9, and after the processing of S11, the CPU 21 determines whether or not the joystick 5a is tilted in the up (U) direction (S12). When the joystick 5a is tilted in the up (U) direction (S12: YES), the CPU 21 determines whether or not the folder of the same hierarchical layer as the present storage destination folder is present (S13).

When the folder of the same hierarchical layer is not present (S13: NO), the processing returns to S12. When the folder of the same hierarchical layer as the present storage destination folder is present (S13: YES), the CPU 21 sets the previous folder of the same hierarchical layer as the storage destination folder, and changes display of the storage destination folder name in the screen 4a (S14).

For example, when the joystick 5a is tilted in the up (U) direction in the state in which the "ENGINE1_SN001" folder is the storage destination folder (state of the screen 52), for example, the "DCIM" folder which is the previous folder of the same hierarchical layer is set as the storage destination folder. That is to say, the screen transitions from the screen 52 to 51. Further, when the joystick 5a is tilted in the up (U) direction, the "ENGINE2_SN002" folder which is the last folder of the same hierarchical layer is set as the storage destination folder since a previous folder of the same hierarchical layer is absent, display of the storage destination folder in the screen 4a is changed, and the screen transitions from the screen 51 to 53.

Likewise, when the joystick 5a is tilted in the up (U) direction in the state of the screen 55 in which the "HPC_STAGE1_ZONE2" folder is set as the storage destination folder, the screen transitions from the screen 55 to the screen 54 in which the "HPC_STAGE1_ZONE1" folder is set as the storage destination folder. Further, when the joystick 5a is tilted in the up (U) direction in the state of the screen 54, the "HPC_STAGE1_ZONE2" folder which is the last folder of the same hierarchical layer is set as the storage destination folder, since the previous folder of the same hierarchical layer is absent. That is to say, the screen transitions from the screen 54 to 55.

The processing of S3 to S14 of the above configures a storage destination folder changing section which changes the storage destination folder in accordance with an operation of the operation section 5. More specifically, the processing of S3 to S14 configures the storage destination folder changing section which changes the storage destination folder in the state in which a live image is displayed, which is the state in which the endoscopic image is displayed on the LCD 4, and is the state in which the live image which is being picked up by the image pickup section provided at the insertion portion of the endoscope is displayed.

Returning to FIG. 5, in the case of NO in S12, and after the processing of S14, the CPU 21 determines whether or not the freeze button is depressed (FIG. 6, S21).

When the freeze button is not depressed (S21: NO), the processing returns to S2. When the freeze button is depressed (S21: YES), the CPU 21 determines whether or not the REC button is depressed (S22). The REC button is a button which performs instruction for storing the frozen image in the storage medium. When the freeze button is depressed, the CPU 21 generates a still image based on the image pickup signal from the image pickup unit 41, and displays the still image on the LCD 4.

The configuration may be adopted, in which when the freeze button is depressed in S21, the storage destination folder can be changed in the freeze state of a live image, as in S3 to S14 in the state in which a live image is displayed.

When the REV button is not depressed, the processing returns to S21 It is determined whether the state in which the freeze button is depressed is continued, in other words, whether the freeze button is released or not. If the freeze button is released (S21: NO), the processing returns to S2.

If the REC button is depressed (S22: YES), the CPU 21 displays a predetermined confirmation message as shown in FIG. 7 on the screen 4a (S23).

Figure 7:
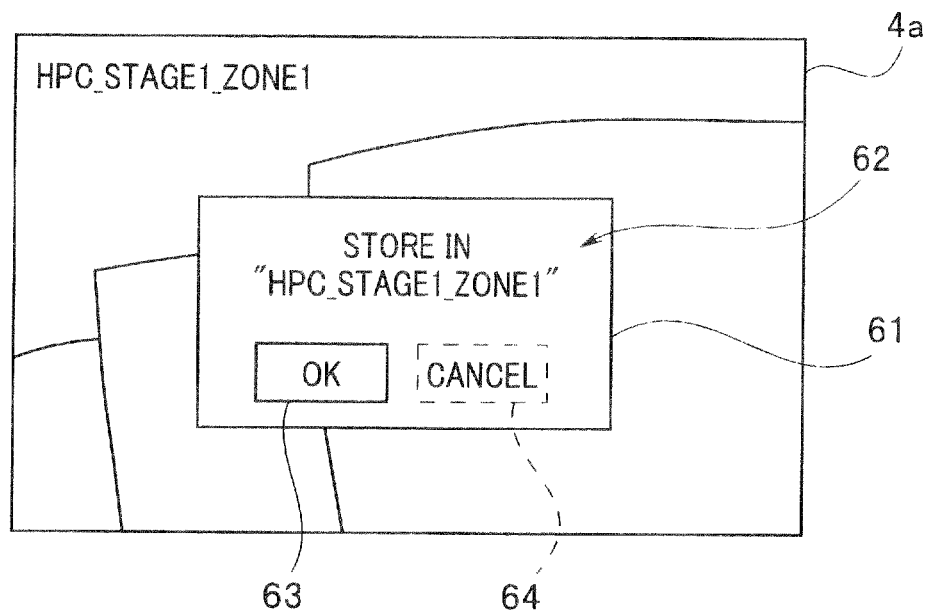
FIG. 7 is a view showing a display example of a confirmation message according to the embodiment of the present invention.

FIG. 7 is a view showing a display example of the confirmation message. On the screen 4a of the LCD 4, a still image by freeze is displayed, and on the screen, a predetermined confirmation message is displayed by a pop-up window 61. FIG. 7 is a display example in the ease of the REC button being depressed in the display state of the screen 54, and a message 62 such as "Store in "HPC_STAGE1_ZONE1"." is displayed in the window 61.

Further, the window 61 also includes an "OK" button 63 and a "cancel" button 64, and the user can select the "OK" button 63 or the "cancel" button 64 by performing a predetermined operation in the operation section 5. In FIG. 7, the "OK" button 63 is in a selected state as default, and therefore, the "OK" button 63 is displayed by being more emphasized than the "cancel" button 64.

The user selects the "OK" button 63 when storing the still image which is obtained by freeze in the folder shown in the confirmation message. However, when the user stores the still image which is obtained by freeze in the folder other than the folder shown in the confirmation message, the user selects the "cancel" button 64.

After S23, the CPU 21 determines whether or not the "OK" button 63 is depressed. When the "OK" button 63 is not depressed, that is, when the "cancel" button 64 is depressed (S24: YES), the CPU 21 erases the window 61 from the screen 4a, and the processing shifts to S25.

A still image by freeze, and the storage destination folder name which is set at present are displayed on the screen 4a. The user can change the storage destination folder by operating the joystick 5a in the screen display state.

Figure 8:
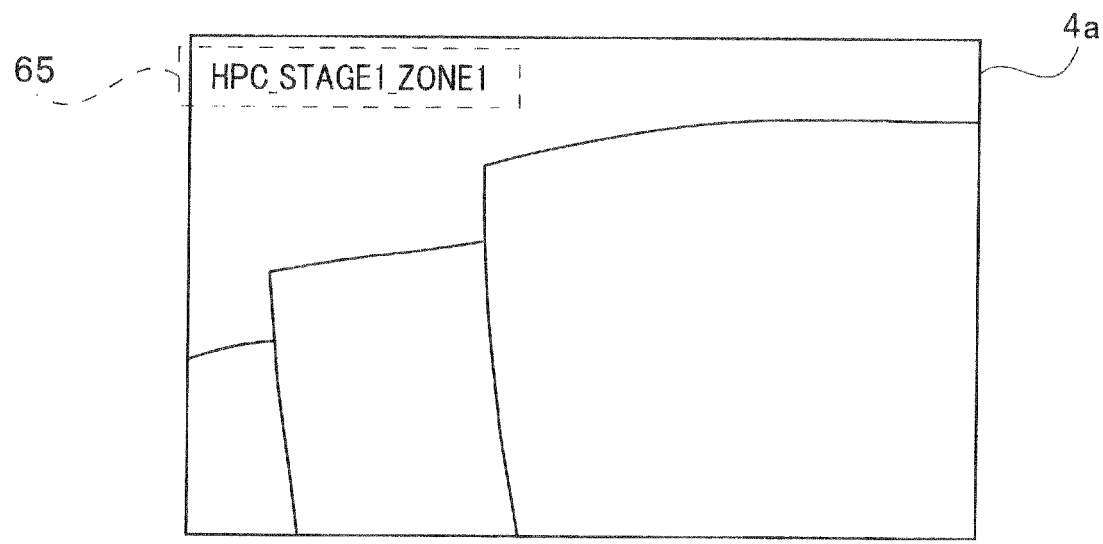
FIG. 8 is a view showing an example of a screen in the case of change of the storage destination folder in a state in which a still image is displayed, according to the embodiment of the present invention.

FIG. 8 is a view showing an example of the screen in the case of the storage destination folder being changed in the state in which a still image is displayed. When the joystick 5a is operated in the state in which the still image displayed by freeze is displayed, the storage destination folder is changed in response to the operation, and only the folder name which is displayed in a storage destination folder display region 65 which displays the storage destination folder changes in the screen 4a, in response to the operation of the joystick 5a. Accordingly, the user causes a desired storage destination folder name to be displayed on the storage destination folder display region 65 by operating the joystick 5a, and can change the storage destination folder.

The processing of S25 configures a storage destination folder changing section which changes a storage destination folder in accordance with an operation of the operation section 5, and also configures a storage destination folder information display section which displays information indicating the storage destination folder in the state in which an endoscopic image is displayed on the LCD 4.

In particular, the processing of S25 configures the storage destination folder changing section which can change the storage destination folder in the state in which a still image is displayed, which is the state in which an endoscopic image is displayed on the LCD 4, and the state in which the still image which is picked up and obtained by the image pickup section provided in the insertion portion of the endoscope is displayed.

As above, in the case of NO in S24, the CPU 21 causes the screen to transition as shown in FIG. 4 in accordance with the tilting operation in the up, down, left and right directions of the joystick 5a, and the user selects and sets a desired folder as the storage destination folder, and changes display of the storage destination folder name in the screen 4a (S25).

It is determined whether or not the REC button is depressed again in the state in which the storage destination folder is set and changed (S26). If the REC button is not depressed (S26: NO), the processing returns to S25.

If the REC button is depressed in S26 (S26: YES), the processing shifts to S23, and the CPU 21 displays a predetermined message for confirmation of the storage destination folder (S23).

When the storage destination folder is confirmed (S24: YES), setting processing of a file mark is performed (S27). The file mark is a predetermined mark which is added to the file name which is stored and functions as an identification symbol.

A file mark is optionally added by the user to show what kind of image the stored image is. A file mark is assigned to the file name in order to classify the images into the kinds such as "Attention required", "No problem" and "Reexamination required", for example. Accordingly, addition of a file mark is performed according to a user's option.

Figure 9:
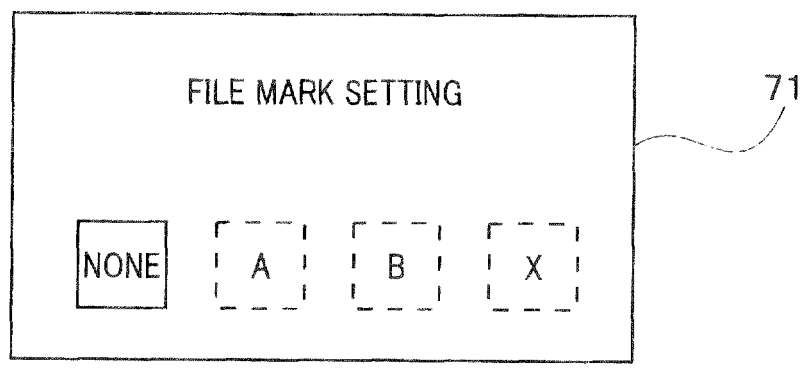
FIG. 9 is a diagram showing a display example of a file mark setting window according to the embodiment of the present invention.

FIG. 9 is a view of a display example of a file mark setting window in setting processing of a file mark.

A window 71 of FIG. 9 is also displayed as a pop-up window on a still image display screen as the window 61. The user can select any one of three kinds (four kinds if "nothing" indicating that nothing is added is included) by performing a predetermined operation in the operation section 5. In the case of FIG. 9, the three kinds of file marks. "A", "B" and "X" can be added. The file mark is not limited to a single character, and may be a character string such as "REPAIR" and "OR", for example.

In the present embodiment, as shown in FIG. 3, the file name is made by addition of a serial number to the folder name of the folder in which the file is stored. For example, the file names of the files which are registered or stored in the file of "HPC_STAGE1_ZONE1" are "HPC_STAGE1_ZONE1_001.jpg" and the like. Accordingly, when the file mark is added, if, for example, the file mark is "A", the file name is "HPC_STAGE1_ZONE1_001_A.jpg", and if the file mark is "X", the file name is "HPC_STAGE1_ZONE1_001_X.jpg".

Accordingly, the user judges the inspection site or the like from the folder name by only looking at the file name, and also can judge the kind of the image.

In FIG. 9, when the window 71 is displayed as a pop-up window, "none" indicating not to add is in the selected state by default. Accordingly, if an operation of giving an instruction of confirmation of selection is performed in the state of FIG. 9, a file mark is not added to the file name. More specifically, the file name becomes "HPC_STAGE1_ZONE1_001.jpg" or the like.

The processing of S27 configures an identification symbol setting section which selects a file mark from a plurality of predetermined file marks and sets the file mark.

Returning to FIG. 6, in the case of YES in S24, the processing shifts to the setting processing of a file mark (S27), and addition processing of the file mark as described above is executed.

Thereafter, the CPU 21 stores an image in the selected or set storage destination folder (S28). More specifically, S28 configures a storage section which stores an endoscopic image in the storage destination folder which is set as the storage destination for an endoscopic image from a plurality of folders which are created in the memory card 11 in advance.

Further, in S28, when a still image of the endoscopic image which is acquired in accordance with the storage instruction from the operation section 5 is stored, the still image is stored in the set or changed storage destination folder after a predetermined confirmation message about the storage destination folder is displayed, and confirmation of the storage destination folder is performed.

Furthermore, in S28, the file mark set in S27 is added to the file name of the endoscopic image, and the endoscopic image is stored in the storage destination folder.

Subsequently, the CPU 21 determines whether or not an end instruction is given (S29), and when the end instruction is given (S29: YES), the processing ends. If the end instruction is not given (S29: NO), the processing shifts to S2.

In the aforementioned embodiment, the joystick is an operation section which is operable in the first direction in the lateral direction, and the second direction in the vertical direction orthogonal to the lateral direction. As for change of the storage destination folder, the storage destination folder is changed by hierarchical layer movement in the vertical direction of the hierarchical structure in accordance with the operation in the lateral direction, and the storage destination folder is changed by movement in the same hierarchical layer of the hierarchical structure in accordance with the operation in the vertical direction. Accordingly, by the operation of the joystick corresponding to the image of the hierarchical structure of the folder, the user can perform transition of the screen.

Furthermore, the operation section for changing the storage destination folder may be a so-called, cruciform key, up, down, right and left keys, or the like. Further, the operation section may be a cruciform key, up, down, left and right keys and the like generated by software, which are displayed on the screen.

Further, in the aforementioned embodiment, the joystick 5a is a dedicated joystick for change or selection of the storage destination folder. However, a joystick for use in a bending operation may be used as the operation device for selection of the storage destination folder under mode switching.

Furthermore, in the aforementioned embodiment, the information indicating the storage destination folder is displayed when a live image is displayed. However, the information indicating the storage destination folder may be displayed only when a freeze button is depressed.

As above, according to the aforementioned embodiment, the endoscope apparatus and the method for storing an endoscopic image can be realized, which enables a user to confirm the storage destination folder when the user stores an endoscopic image, and enables the user to change the storage destination folder easily.

The present invention is not limited to the aforementioned embodiment, and various modifications, alterations and the like can be made within the range without changing the gist of the present invention.

The invention claimed is:

1. An endoscope apparatus, comprising:
a display section which displays an endoscopic image;
an operation section which is operable to input a storage instruction to store the endoscopic image;
a storage section which stores the endoscopic image in a storage destination folder which is set as a storage destination for the endoscopic image from among a plurality of folders which are created in a storage device in advance;
a storage destination folder information display section which displays information indicating the storage destination folder in a state in which the endoscopic image is displayed on the display section; and
a storage destination folder changing section which changes the storage destination folder, which is set as the storage destination for the endoscopic image to be stored when the storage instruction is input through the operation section, in response to an operation of the operation section before the input of the storage instruction, while the endoscopic image is displayed on the display section.

2. The endoscope apparatus according to claim 1, wherein the display section displays a live image before the input of the storage instruction, wherein the live image is picked up by an image pickup section provided in an insertion portion of an endoscope, and wherein the storage destination folder changing section is configured to change the storage destination folder in the state in which the live image is displayed in response to an operation of the operation section before the input of the storage instruction.

3. The endoscope apparatus according to claim 2, wherein the storage section stores a still image of the endoscopic image in the storage destination folder after a confirmation message concerning the storage destination folder is displayed, and the storage destination folder is confirmed when the storage section stores the still image of the endoscopic image which is acquired in accordance with the storage instruction from the operation section.

4. The endoscope apparatus according to claim 1, wherein the storage section decides a file name of a still image of the endoscopic image based on a folder name of the storage destination folder when the storage section stores the still image of the endoscopic image which is acquired in accordance with the storage instruction from the operation section.

5. The endoscope apparatus according to claim 1, wherein the storage section adds an identification symbol to a file name of the endoscopic image, and stores the endoscopic image in the storage destination folder.

6. The endoscope apparatus according to claim 5, further comprising:
an identification symbol setting section which selects the identification symbol from a plurality of predetermined identification symbols, and sets the identification symbol,
wherein the storage section adds the identification symbol set by the identification symbol setting section to the file name of the endoscopic image.

7. The endoscope apparatus according to claim 1, wherein the plurality of folders created in the storage device include a hierarchical structure.

8. The endoscope apparatus according to claim 7, wherein the operation section comprises an operation section which is operable in a first direction and a second direction orthogonal to the first direction, and the storage destination folder changing section changes the storage destination folder by hierarchical movement in a vertical direction of the hierarchical structure in response to an operation in the first direction, and changes the storage destination folder by movement in a same hierarchical layer of the hierarchical structure in response to an operation in the second direction.

9. The endoscope apparatus according to claim 8, wherein:
the operation section is operable in a lateral direction and a vertical direction,
the first direction comprises one of the lateral direction and the vertical direction, and the second direction comprises the other of the lateral direction and the vertical direction,
the storage destination folder changing section changes the storage destination folder by hierarchical movement in the vertical direction of the hierarchical structure in response to an operation of the operation section in said one of the lateral direction and the vertical direction, and changes the storage destination folder by movement in a same hierarchical layer of the hierarchical structure in response to an operation of the operation section in the other of (i) the lateral direction and the vertical direction.

10. The endoscope apparatus according to claim 9, wherein the operation section comprises one of (i) a joystick, (ii) a cruciform key, and (iii) left, right, up, and down keys.

11. The endoscope apparatus according to claim 7, wherein the storage destination folders in a same hierarchical layer are sorted in order of a date and time when the storage destination folders are created.

12. The endoscope apparatus according to claim 1, wherein the operation section comprises a touch panel which is provided together with the display section.

13. The endoscope apparatus according to claim 1, wherein the storage device is a storage medium attachable to and detachable from the endoscope apparatus.

14. The endoscope apparatus according to claim 1, wherein:
the storage instruction made via the operation section includes an instruction for generating a still image of the endoscopic image and an instruction for storing the still image, the instruction for storing the still image being made after the instruction for generating the still image, and
the storage section stores the still image in the storage destination folder which is set as the storage destination.

15. A method for changing a storage destination folder for an endoscopic image, comprising:
displaying an endoscopic image picked up by an endoscope apparatus in a display section;
displaying information indicating a storage destination folder which is set as a storage destination for the endoscopic image from among a plurality of folders which are created in a storage device in advance, in a state in which the endoscopic image is displayed on the display section;
changing the storage destination folder, which is set as the storage destination for the endoscopic image to be stored when the storage instruction is input through the operation section, in response to an operation of an operation section before input of a storage instruction via the operation section, while the endoscopic image is displayed on the display section; and storing the endoscopic image in the storage destination folder according to the input of the storage instruction.

16. The method for changing a storage destination folder for an endoscopic image according to claim 15, wherein displaying the endoscopic image on the display section includes displaying a live image which is picked up by an image pickup section provided in an insertion portion of an endoscope.

17. The method for changing a storage destination folder for an endoscopic image according to claim 16, wherein a still image of the endoscopic image is stored in the storage destination folder after a confirmation message concerning the storage destination folder is displayed, and the storage destination folder is confirmed when the still image of the endoscopic image which is acquired in accordance with a storage instruction from the operation section is stored.

18. The method for changing a storage destination folder for an endoscopic image according to claim 15, wherein an identification symbol is added to a file name of the endoscopic image when the endoscopic image is stored in the storage destination folder.

19. The method for changing a storage destination folder for an endoscopic image according to claim 18, wherein the identification symbol is selected from a plurality of predetermined identification symbols, and is set.

20. The method for changing a storage destination folder for an endoscopic image according to claim 15, wherein the plurality of folders created in the storage device include a hierarchical structure.

21. The method for changing a storage destination folder for an endoscopic image according to claim 20, wherein the operation section comprises an operation section which is operable in a first direction and a second direction orthogonal to the first direction, and the storage destination folder is changed by hierarchical movement in a vertical direction of the hierarchical structure in response to an operation in the first direction, and the storage destination folder is changed by movement in a same hierarchical layer of the hierarchical structure in response to an operation in the second direction.

22. The method for changing a storage destination folder for an endoscopic image according to claim 15, wherein the storage device is a storage medium attachable to and detachable from the endoscope apparatus.

23. The method for changing a storage destination folder for an endoscopic image according to claim 15, wherein:

the storage instruction made via the operation section includes an instruction for generating a still image of the endoscopic image and an instruction for storing the still image, the instruction for storing the still image being made after the instruction for generating the still image, and the still image is stored in the storage destination folder which is set as the storage destination.

* * * * *